(12) United States Patent
Drmanac et al.

(10) Patent No.: US 11,761,040 B2
(45) Date of Patent: Sep. 19, 2023

(54) DNA PROTECTION AGENT IN DNA IMAGING BUFFER

(71) Applicant: MGI Tech Co., Ltd., Shenzhen (CN)

(72) Inventors: Snezana Drmanac, Los Altos Hills, CA (US); Matthew J. Callow, San Jose, CA (US); Radoje T. Drmanac, Los Altos Hills, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 0 days.

(21) Appl. No.: 17/600,826

(22) PCT Filed: Apr. 19, 2021

(86) PCT No.: PCT/CN2021/088114
§ 371 (c)(1),
(2) Date: Oct. 1, 2021

(87) PCT Pub. No.: WO2021/213321
PCT Pub. Date: Oct. 28, 2021

(65) Prior Publication Data
US 2023/0033699 A1 Feb. 2, 2023

Related U.S. Application Data

(60) Provisional application No. 63/012,836, filed on Apr. 20, 2020.

(51) Int. Cl.
*C12P 19/34* (2006.01)
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 5,912,241 A | 6/1999 | Gottlieb et al. | |
| 6,544,797 B1 | 4/2003 | Buechler et al. | |
| 6,979,829 B2 | 12/2005 | Calvert et al. | |
| 7,883,869 B2 | 2/2011 | Ju et al. | |
| 7,993,895 B2 | 8/2011 | Eid et al. | |
| 7,998,717 B2* | 8/2011 | Eid ...................... | A61K 38/446 424/94.1 |
| 8,071,346 B2 | 12/2011 | Eid et al. | |
| 8,551,702 B2 | 10/2013 | Drmanac et al. | |
| 9,163,053 B2 | 10/2015 | Siddiqi et al. | |
| 9,222,132 B2 | 12/2015 | Drmanac | |
| 9,791,409 B2 | 10/2017 | Gordon et al. | |
| 10,023,910 B2 | 7/2018 | Drmanac et al. | |
| 10,093,974 B2 | 10/2018 | Beechem et al. | |
| 10,106,851 B2 | 10/2018 | Klausing et al. | |
| 10,851,410 B2 | 12/2020 | Drmanac et al. | |
| 11,162,129 B2 | 11/2021 | Andruzzi et al. | |
| 2007/0128133 A1* | 6/2007 | Eid ...................... | A61K 38/446 424/59 |
| 2010/0255487 A1 | 10/2010 | Beechem et al. | |
| 2013/0189684 A1* | 7/2013 | Ehrich ................. | C12Q 1/6886 435/6.11 |
| 2015/0132331 A1* | 5/2015 | Lu ......................... | A61K 39/12 435/69.3 |
| 2017/0119865 A1 | 5/2017 | Lee et al. | |
| 2017/0233796 A1* | 8/2017 | Olejnik ............... | C12Q 1/6823 435/6.11 |
| 2018/0327829 A1 | 11/2018 | Mir | |

FOREIGN PATENT DOCUMENTS

| | | |
|---|---|---|
| CN | 103667432 A | 3/2014 |
| CN | 109295168 A | 2/2019 |
| WO | 2018119057 A2 | 6/2018 |
| WO | 2020060937 A1 | 3/2020 |

OTHER PUBLICATIONS

PCT/CN2021/088114, "International Search Report and Written Opinion", dated Jul. 23, 2021, 9 pages.
Chinese Application No. 202180003243.9, Notice of Decision to Grant dated Dec. 2, 2022, 5 pages (4 pages of Original Document and 1 page of English Translation).
International Application No. PCT/CN2021/088114, International Preliminary Report on Patentability dated Nov. 3, 2022, 6 pages.
Australian Patent Application AU2006320414B2, "Mitigation of photodamage in analytical reactions", Jan. 12, 2006, 51 pages, PCT publication WO2007/064905A2 starting on p. 2, Applicant, Pacific Biosciences of California, Inc.
Drmanac et al., "Human Genome Sequencing Using Unchained Base Reads on Self-Assembling DNA Nanoarrays", Science, Jan. 1, 2010, pp. 78-81, vol. 327, Issue 596.
Fischer-Nielsen et al., "8-hydroxydeoxyguanosine in vitro: effects of glutathione, ascorbate, and 5-aminosalicylic acid", Free Radical Biology & Medicine, Aug. 1992, pp. 121-126, vol. 13, Issue 2.
Hahn et al., "CoolMPS for robust sequencing of single-nuclear RNAs captured by droplet-based method", Nucleic Acids Research, Jan. 25, 2021, pp. 1-12, vol. 49, No. 2.
Levy et al., "Advancements in Next-Generation Sequencing", Ann Rev Genom Hum Genet., Jun. 9, 2016, pp. 95-11, 17.
Li et al., "CoolMPS: evaluation of antibody labeling based massively parallel non-coding RNA sequencing", Nucleic Acids Research, Jan. 25, 2021, pp. 1-13, vol. 49, No. 2.
Mardis, "DNA sequencing technologies: 2006-2016", Nat Protoc., Jan. 5, 2017, pp. 213-218, 12(2).
Murigneux et al., "Comparison of long-read methods for sequencing and assembly of a plant genome", GigaScience, Dec. 2020, pp. 1-11, vol. 9, Issue 12.
Shendure et al., "DNA sequencing at 40: past, present and future", Nature, 2017, pp. 345-353, 550 (7676).
Van Dijk et al., "The Third Revolution in Sequencing Technology", Trends Genetics, Sep. 2018, pp. 666-681, vol. 34, Issue 9.

(Continued)

*Primary Examiner* — Kenneth R Horlick
(74) *Attorney, Agent, or Firm* — Kilpatrick Townsend & Stockton LLP (57) ABSTRACT

Methods and compositions for protecting DNA from light-induced damage and other modifications that occur during DNA sequencing using fluorescent dyes are disclosed.

16 Claims, 3 Drawing Sheets

(56) References Cited

OTHER PUBLICATIONS

Wang et al., "Efficient and unique cobarcoding of econdgeneration sequencing reads from long DNA molecules enabling cost-effective and accurate sequencing, haplotyping, and de novo assembly", Genome Research, Apr. 2, 2019, pp. 798-808.
Yu et al., "Reactive oxygen species-induced DNA damage and its modification: a chemical investigation", Mutat Res., Oct. 6, 1997, pp. 201-210, 379(2).
Zheng et al., "The contribution of reactive oxygen species to the photobleaching of organic fluorophores", Photochem Photobiol., Mar.-Apr. 2014, pp. 448-454, 90(2).

* cited by examiner

DNA PROTECTION AGENT IN DNA IMAGING BUFFER

REFERENCE TO PREVIOUS APPLICATION

This application is a 35 USC § 371 U.S. National Stage application of PCT Application No. PCT/CN2021/088114, filed Apr. 19, 2021, which claims the priority benefit of U.S. provisional patent application 63/012,836, filed Apr. 20, 2020, the entire content of which is incorporated herein by reference for all purposes.

BACKGROUND

Many DNA sequencing methods and other analytical methods involve incorporation of a fluorescently labeled nucleotide into a polynucleotide, and detection of the incorporation based on a fluorescent signal produced upon illumination of the polynucleotide by an excitation wavelength. For example, sequencing-by-synthesis methods involve multiple cycles of incorporation of labeled nucleotides by primer extension, illumination of the labeled nucleotides, and detection of fluorescent signals. It has been observed that this process damages the extended primer and/or polynucleotide template, limiting read length and reducing accuracy of long reads.

BRIEF SUMMARY OF THE INVENTION

This disclosure provides methods and compositions for protecting DNA from light-induced damage and other modifications that-occur during DNA sequencing using fluorescent dyes. In a reaction done under standard conditions, the damage accumulated during 20 or 95 cycles of sequencing-by-synthesis results in signal loss of as much as 50%. By protecting the DNA template and growing strand with an imaging buffer during the imaging step in each cycle, the signal loss for the same number of cycles can be minimized to less than 10%.

The description below provides more details of a method of massively parallel nucleic acid sequencing. The method may include carrying out at least 20 nucleic acid sequencing cycles using an array comprising immobilized DNA templates at predetermined positions on the array. Each cycle comprises: i) incorporating reversible terminator nucleotides into a plurality of growing strands or extended primers on the array, wherein the fluorescent dye molecules are associated with the incorporated reversible terminator nucleotides before or after incorporation; ii) contacting the array with an imaging buffer comprising 5 to 200 mM reduced L-glutathione, wherein the imaging buffer has a pH of from about 7.5 to about 9; iii) illuminating the array to induce fluorescent emission from the fluorescent dye molecules and detecting the fluorescent emission; and then iv) removing the imaging buffer and the fluorescent dye molecules from the array. When using the imaging buffer, the accumulated signal loss is reduced compared to signal loss that occurs without the imaging buffer.

In step (iv) the imaging buffer and the fluorescent dye molecules may be removed at the same time. The fluorescent dye may be conjugated to the incorporated reversible terminator nucleotides. The fluorescent label may be attached to affinity reagents that bind the incorporated reversible terminator nucleotides. The affinity reagents may be monoclonal antibodies. The imaging buffer may also include trolox at a concentration of 0.5 to 25 mM, preferably 2 to 4 mM. The concentration of glutathione in the imaging buffer may be 10 to 500 mM, preferably 100 mM. The pH of the imaging buffer may be about 7.5 to about 9.0. The detection or imaging may be performed at a temperature of about 50° C.

The immobilized DNA templates may be in the form of DNA nanoballs (DNB), each having multiple copies of a template sequence. Alternatively, the DNA templates may be in the form of a clonal cluster of DNA strands, each typically having one copy of a template sequence. At least 20, 50, 100, 200, 300, 400, 500, or 1000 cycles of sequencing may be performed.

The protective effect of the imaging buffer can be quantified by comparing the intensity of fluorescence emission after a certain number of cycles with the intensity earlier on or at the beginning. By way of illustration, the fluorescence emission measured in the 20th sequencing cycle may be at least 90% of the emission measured in the first cycle. The decrease in emission measured in the 20th sequencing cycle relative to the emission in the first cycle in the presence of reduced L-glutathione may be less than 50% the decrease measured in the 20th sequencing cycle relative to the emission in the first cycle in the absence of reduced L-glutathione.

This disclosure also provides an imaging buffer for use in DNA sequencing, the imaging buffer comprising reduced L-glutathione, wherein the pH of the buffer is between about 7.5 and about 9. The imaging buffer may further comprise trolox, typically at a concentration of 0.5 to 25 mM, or 2 to 4 mM, optionally including buffering reagents, solubilizers, and other components in any combination. By way of illustration, the imaging buffer may comprise 1000 mM Tris buffer, 400 mM NaCl, 0.05 polyethylene glycol sorbitan monolaurate, 4 mM trolox, and 100 mM reduced glutathione, buffered at pH 7.5 to 9.0. An imaging buffer of this kind can be used to improve nucleic acid sequencing to sustain emission intensity of fluorescent dyes used in the sequencing through multiple cycles of sequencing. Typically, at least 20 cycles of the sequencing are performed by (a) incorporating reversible terminator nucleotides into a plurality of growing strands on the array, wherein fluorescent dye molecules are associated with the incorporated reversible terminator nucleotides before or after incorporation, and then (b) illuminating the array to induce fluorescent emission from the fluorescent dye molecules and detecting the fluorescent emission. The method of synthesis is improved by conducting the illuminating and optionally the incorporating of the reversible terminators in an imaging buffer formulated in accordance with this disclosure.

This disclosure also provides a reaction mixture for use in DNA sequencing, the mixture comprising a single-stranded DNA template, a fluorescent dye, and any of the herein-described imaging buffers.

This disclosure also provides a kit comprising (a) an imaging buffer described herein a first container and, in at least one additional container, (b1) reversible terminator nucleotides (rt-dNTPs) at least some of which comprise fluorescent dyes attached thereto, or (b2) reversible terminator nucleotides (rt-dNTPs) and affinity reagents, optionally monoclonal antibodies, that comprise fluorescent dyes attached thereto, or (b3) reversible terminator nucleotides (rt-dNTPs), primary affinity reagents, and secondary affinity reagents that comprise fluorescent dyes attached thereto.

Other aspects of the invention are provided in the description that follow, the accompanying drawing, and the appended claims.

BRIEF DESCRIPTION OF THE DRAWING

FIGS. 1A and 18 show that an imaging buffer according to this disclosure protects single-stranded DNA (ssDNA)

from laser damage during imaging of fluorescent dye being used to sequence the ssDNA. In FIG. 1A, the imaging buffer was formulated to protect the ssDNA template using the protective agent glutathione. In FIG. 1B, the imaging buffer contained no protective ingredients.

DETAILED DESCRIPTION

Disclosed herein are methods and compositions for improving results obtained in DNA sequencing. Without intending to be bound by a particular mechanism, the use of imaging buffers containing the combination of reduced L-glutathione and trolox (6-hydroxy-2,5,7,8-tetramethyl-chroman-2-carboxylic acid), protects single-stranded DNA templates and extended primers against damage that occurs during the process of imaging (e.g., laser excitation of fluorescent dyes associated with the templates and extended primers). This damage reduces signal and limits read-length. Without intending to be bound by a particular mechanism, the use of imaging buffers containing the combination of reduced L-glutathione and trolox reduces such damage (i.e., "protects" the templates and extended primers) extending read length and improving accuracy of DNA sequencing.

Terms

As used herein, a fluorescent dye is "associated" with a nucleic acid (e.g., templates and extended primers) when the fluorescent dye is brought into physical proximity to the nucleic acid, as in sequencing (e.g., sequencing-by-synthesis). For illustration and not limitation, two common methods for associating a fluorescent dye are (1) by linking the dye to an rt-dNTP (e.g., via a cleavable linker) and incorporating the rt-dNTP into the extended primer and (2) by incorporating a non-labeled reversible terminator nucleotide (NLRT-dNTP) into the extended primer and binding a fluorescently labeled affinity reagent to the incorporated NLRT nucleotide.

As used herein, the terms "L-reduced glutathione", "reduced L-glutathione", "L-glutathione reduced" and "reduced glutathione" have the same meaning, and are used interchangeably in this disclosure and the priority document to refer to reduced L-glutathione.

As used herein, "primer extension product," "extension product," "extended primer," and "growing strand," have the same meeting and refer to the primer extension produce produced by adding nucleotides to a primer annealed to the template (e.g., first sequencing cycle) or to an extended primer produced during a subsequent sequencing cycle.

"MPS" means "massively parallel sequencing."

As used herein, the terms "fluorescent" and "fluorescence" are used interchangeably.

As used herein, the terms "fluorescent dye," "fluorescent label," and "fluorophore" are used interchangeably and refer to a fluorescent chemical compound, i.e., a compound that absorbs light energy of a specific wavelength and re-emits light at a longer wavelength.

The term "signal loss" refers to a pro decrease in fluorescence emission intensity from primer extension products produced from a clonal population of templates in the course of multiple cycles of primer extension and imaging. "Signal loss" is also referred to as "laser-induced degradation" or "laser-induced damage" to DNA are used interchangeably and refer to the progressive loss of fluorescent signal (signal loss) that occurs during with increasing numbers of illumination cycles during DNA sequencing.

The terms "about" and "approximately" as used herein shall generally mean an acceptable degree of error for the quantity measured given the nature or precision of the measurements. Typically, exemplary degrees of error are within 10%, and more preferably within 5% of a specified value or range of values.

Overview

As noted above, we have discovered that, unexpectedly, use of an imaging buffer containing reduced L-glutathione and trolox (6-hydroxy-2,5,7,8-tetramethylchroman-2-carboxylic acid) during the illumination step of a cyclical sequencing-by-synthesis process protects DNA templates and/or extended primers from damage.

Many methods of DNA sequencing involve associating a fluorescent dye with a polynucleotide (e.g., template and extended primer). Multiple sequencing cycles are carried out in which the fluorescent dye is illuminated in each cycle at a wavelength (excitation wavelength) that causes emission of light at a different wavelength (emission wavelength). The illumination can be said to "induce" the fluorescent emission. Fluorescent dyes are used in a variety of sequencing methods, including sequencing-by-synthesis, sequencing by hybridization, sequencing by ligation, and cPAL (U.S. Pat. No. 8,551,702). The present disclosure is focused on massively parallel sequencing-by-synthesis using reversible terminator dNTPs, but the methods, imaging buffers, and other reagents described can be used in a variety of sequencing applications.

Methods of massively parallel sequencing-by-synthesis using reversible terminator dNTPs are well known in the art and are amply described in the scientific and technical literature. See, for example, Drmanac et al. "Nucleic acid sequencing using affinity reagents" U.S. Pat. No. 10,851,410 and publication No. 20180223358A1; Drmanac et al. (2020) "CoolMPS™: Advanced massively parallel sequencing using antibodies specific to each natural nucleobase" bioRxiv doi: doi.org/10.1101/2020.02.19.953307; Shendure et al., "DNA sequencing at 40: past, present and future" Nature 550 (7676):345-353; Metzker, 2010, "Sequencing technologies—the next generation," Nat Rev Genet, 11:31-46; Guo et al., 2010 "An integrated system for DNA sequencing by synthesis using novel nucleotide analogues" Acc Chem Res, 43:551-563; van Dijk et al., 2018, "The Third Revolution in Sequencing Technology Trends Genet 34(9):666-681"; Mardis (2017) DNA sequencing technologies: 2006-2016," Nat Protoc. 12(2):213-218; and Levy and Myers, 2016, "Advancements in Next-Generation Sequencing" Annual Review of Genomics and Human Genetics 2016 17:1, 95-115; the entire disclosures of which are herein incorporated by reference.

Sequencing-by-synthesis methods are well known and may include the following steps:

i) providing an array (typically in a flow cell) of immobilized DNA templates. Typically the DNA templates are at predetermined positions on the array;

ii) annealing primers to the immobilized templates (typically the immobilized templates are single-stranded DNA templates. In some embodiments immobilized templates are made single-stranded by in situ denaturation;

iii) carrying out multiple cycles of:

a) extending the primers in an extension buffer containing a DNA polymerase in the presence of reversible terminator deoxyribonucleotides (rt-dNTPs), thereby producing extended primers annealed to the DNA templates. The extended primers are or can be associated with a fluorescent dye(s);

b) removing the extension buffer and contacting the array with imaging buffer (optionally washing away the extension buffer before flooding the array with imaging buffer);

c) illuminating the array to induce fluorescent emission from the fluorescent dye(s) molecule(s);

d) acquiring images showing the pattern of fluorescent emission; and e) removing the imaging buffer and fluorescent dye(s), and removing the blocking moiety of the incorporated reversible terminator to allow further cycles of primer extension.

Certain aspects of these steps will be described in more detail.

Steps (i) and (III: Providing an array (typically in a flow cell) of immobilized DNA templates. (Typically the DNA templates are at predetermined positions on the array); and annealing primers to the immobilized templates (typically the immobilized templates are single-stranded DNA templates).

In one approach, DNA templates are present on an array, e.g. a microarray or nanoarray. In typical embodiments, the array is present within a flow cell, a fluidic device that delivers reagents (such as the imaging buffer) to the arrayed DNA templates. Exemplary DNA templates used in the present methods can be any single-stranded DNA template suitable for use in the sequencing method involved. In some embodiments, the DNA templates are a clonal population of DNA templates. Typically templates are produced by amplification, including templates generated by PCR, by emulsion PCR, by bridge amplification, by rolling circle amplification, or other methods. Exemplary DNA templates include DNA nanoballs (DNBs) (linear concatemers of DNA monomers generated by rolling circle replication). See, Drmanac et al. (2010) Science 327:78-81. In some embodiments, the templates used for the DNA sequencing comprise ordered arrays of DNBs. Typically, the array surface comprises an ordered array of discrete spaced apart regions (or "spots"), each of which captures a DNB. In some embodiments, the DNBs are 1,000-50,000 nucleotides in length.

Other exemplary DNA templates include clonal clusters of template sequences (e.g., adaptored template sequences), which may be produced by amplification, e.g., bridge amplification and other amplification methods. See, e.g., U.S. Patent Publ. Nos. 2008/0009420 and 2007/0128624, and references listed above.

The DNA templates may be a variety of lengths. In some embodiments the DNA template sequence is a monomer of a DNB. In some embodiments the DNA template sequence is PCR amplicon. For example, in some embodiments, the DNA templates are from 250-2000 nucleotides in length. In particular embodiments, the DNA templates are from about 250 to about 1,000 nucleotides in length.

Step (iii)(a): Extending the primers in an extension buffer containing a DNA polymerase in the presence of reversible terminator deoxyribonucleotides (rt-dNTPs), thereby producing extended primers annealed to the DNA templates. The extended primers are associated with, or can be associated with, a fluorescent dye(s).

A "reversible terminator deoxyribonucleotide (rt-dNTP)" is a modified nucleotide analog that reversibly terminates primer extension when incorporated into a primer extension product (an extended primer). Generally, a reversible terminator nucleotide has a "removable blocking group," a chemical moiety attached to the nucleotide sugar (e.g., deoxyribose), usually at the 3'-O position of the sugar moiety, which prevents addition of a nucleotide by a polymerase at that position. A removable blocking group can be removed enzymatically (e.g., using a phosphatase or esterase), chemical reaction, heat, light, etc., to provide a hydroxyl group at the 3'-position of the nucleoside or nucleotide such that further addition of a nucleotide by a polymerase may occur. The terms "removable blocking group," of a reversible terminator nucleotide may also be referred to as a "reversible blocking group," a "blocking moiety," a "blocking group," "reversible terminator blocking group" and the like. Exemplary blocking groups include 3'-O-azidomethyl, 3'-O-allyl, and others described in U.S. Pat. No. 10,851,410. Also see U.S. Pat. No. 7,771,973.

Other reversible terminator nucleotides include 3'-unblocked reversible terminators (see Wu et al., 2015, "Photocleavable labeled nucleotides and nucleosides and methods for their use in DNA sequencing," U.S. Pat. No. 8,969,535).

The incorporated rt-dNTPs may be directly fluorescently labeled. For example a fluorophore may be covalently linked, to the nucleobase, terminal phosphate, or another part of the rt-dNTPs. See, e.g., U.S. Pat. Nos. 7,771,973; 9,670,539; 10,059,986; and 10,513,731; European patent 3091026 B1; and J. Guo et al. Proc. Natl. Acad. Sci. 2008, 105, 9145-9150. The fluorophore may be connected to the nucleotide by a cleavable linker.

Alternatively, incorporated rt-dNTPs may be unlabeled and bound by an affinity reagent (e.g., antibody) that is fluorescently labeled, whereby the fluorescent dye molecule(s) become associated with the template and extended primer. In one approach, unlabeled rt-dNTPs are incorporated and fluorescently labeled affinity agents, such as monoclonal antibodies or aptamers, are directly or indirectly bound to the incorporated 3' terminal nucleotides. See, Drmanac et al. "CoolMPS™:" Advanced massively parallel sequencing using antibodies specific to each natural nucleobase", BioRxiv (2020), and U.S. Pat. No. 10,851,410. In another example, in sequencing by ligation methods, the dye can be associated with a probe by virtue of it being linked to the 5' end of the probe.

Step (iii)(b): Removing the extension buffer and contacting the array with imaging buffer. After the fluorescent dye is associated with the growing strand, for example, by incorporation of a labeled rt-dNTP or binding of a labeled affinity agent to an incorporated unlabeled rt-dNTP, an imaging buffer is introduced, and the fluorescent dye is illuminated. As discussed in the Examples, we have discovered that certain imaging buffer compositions can significantly reduce signal loss. In one approach this involves washing away the extension buffer and flooding the array with an imaging buffer. In one approach the imaging buffer is used to wash away the extension buffer and reagents. In another approach the extension buffer and reagents are removed in a first buffer exchange, followed by addition of the imaging buffer.

Step (iii)(c): Illuminating the array to induce fluorescent emission from the fluorescent dye(s) molecule(s). Illumination of fluorescent dyes may be performed using one or more lasers. The one or more lasers can be selected to emit light at wavelengths corresponding to the peaks of the excitation spectra of the fluorophores used. The lasers are typically used with one or more cutoff or bandpass filters. Exemplary types of lasers include argon ion, DPSS, OPSL, diode lasers, other lasers and other lasers suitable for DNA sequencing. Lasers may be used at any power, e.g., from 5 mW-2 W. The illumination in each cycle can be any suitable duration, e.g., 10, 20, 30, 40, 50, 60, 70, 80, 90, 100, 110, 120, 130, 140, or 150 ms. One of skill in the art can readily determine the optimal lasers to be used and the conditions for their use, e.g., in view of the type of DNA sequencing performed, the fluorescent dyes used, the nature of the DNA template, the nature of the array, the number of cycles, and the like. A fluorescent dye may be illuminated at a wavelength that is absorbed by the fluorophore, inducing an excited electronic singlet state. The fluorophore then emits light at a different, longer wavelength as it returns to the ground state. For example, the illumination can be performed with light ranging from 300 to 1000 nm, or from 300-400, 400-500, 500-600, 600-700, or 700-800 nm. In one embodiment, four wavelengths, corresponding to 4 dyes, are used, e.g., about 488 nm, about 514 nm, about 532 nm, and about 640 or 660 nm. One of skill in the art can readily determine the optimal wavelength or wavelengths to be used for sequencing, in view of the fluorescent dye or dyes used. See, e.g., Fluorescence Microscopy and Fluorescent Probes, Slavik (Ed.), Springer US, 1996; Fluorescence Spectroscopy (Pesce et al., Eds.), Marcel Dekker, New York, 1971; Haugland, Handbook of Fluorescent Probes and Research Chemicals, Molecular Probes, Eugene, 2005; Fluorescence Microscopy, From Principles to Biological Applications, 2nd Ed., (Kubitscheck, Ed.), Wiley-VGH, 2017; the entire disclosures of which are herein incorporated by reference.

Any fluorophore suitable for use in DNA sequencing can be used, including dyes are listed in WO 2013/044018 (including DEG527, Dy681, DEG527, Atto532, Atto465, 488, 495/Atto514, 520, 532, 550, 565; Atto 520, 532, 550/Atto565, 590, 594, Rhol 1, Rho 12, Rho 13; Atto 647, 655, 665/Atto 680, 700, 725; Alexa 647, 660, Cy5/Alexa 680, 700, Cy5.5; Alexa532, Cy3/Alexa555, 556, 578, 590, Cy3.5; Alexa 488/Alexa532, 555, 556, 578; Dy 647, 648, 649, 650, 651, 652, 654/Dy675, 676, 677, 678, 679, 680, 681, 682, 700, 701, 703, 704; Dy490, 495, 505/Dy530, 547, 548, 549, 550, 554,555, 556, 560; Dy530, 547, 548, 549, 550, 554,555, 556, 560/Dy590, 591, 594, 605, 610, 6150 rhodamine dyes, cyanine dyes (e.g., Cy 3, Cy 5), fluorescein (FITC), Alexa Fluor dyes (Invitrogen/Molecular Probes), BODIPY FL™ (Invitrogen/Molecular Probes), coumarin, Oregon Green, Pacific Blue, Pacific Orange, Yakima Yellow, Texas Red, pyrene, Atto™ (ATTO-Tec), Eterneon™ (BaseClick), Dy™ (Dynomics GmbH), Oyster™ (Luminartis), Abberior™ (Abberior GmbH), Chromeo™ (Active Motif), FAM™ (e.g., 5-Fam™, 6-Fam™), joe, Liz™, Tamra™, Vic™, HEX (e.g., 6-HEX), CAL Fluor (e.g., CAL Fluor Green 520, Gold 540, Orange 560, Red 590, Red 610, Red 615, Red 635), or any form, derivative or analog of any of these dyes. Selection of suitable dyes and guidance as to their use in DNA sequencing is well known in the art. Many dyes can be obtained from a number of commercial sources, for example, from Invitrogen (Molecular Probes), ATTO-Tec, BaseClick, Dynomics GmbH, Luminartis, Abberior, Active Motif, iba, biomers, or Rockland. Modified nucleotides comprising a fluorescent moiety suitable for use with this invention are described, for example, in U.S. Pat. Nos. 7,057,026 and 10,513,731; and in pre-grant publication US 2019/0144482 A1.

The illumination of the dye is typically performed at room temperature, e.g. at 20° C. to 30° C., such as 20° C. to 25° C. In some applications the illumination of the dye is performed at an elevated temperature, e.g., 30° C. to 60° C., such as 40° C. to 60° C., for example to support concurrent biochemical reactions or to minimize the time of temperature ramping from previous or later biochemical reactions. It will be understood that conditions in which localized heating may occur at array positions due to the illumination (e.g. laser) light energy will be avoided.

Step (iii)(d): The fluorescence (fluorescent signal) emitted from positons on the array can be detected (e.g., using a microscope fitted with a charge-coupled device (CCD) camera) and recorded electronically. The pattern of fluorescent emissions from the illuminated array constitutes an "image" which is collected and stored for computer analysis.

Step (iii)(e): Removing the imaging buffer and fluorescent dye(s), and removing the blocking moiety of the incorporated reversible terminator to allow further cycles of primer extension. Following illumination and detection of the fluorescence emitted by the dye, the reversible terminator blocking moiety and fluorophore are removed to prepare the product for a subsequent sequencing cycle. Removal may be achieved in a number of art known methods, including by cleaving phosphine-liable linkers of a labeled rt-PCR. Labeled affinity reagents may be removed, and 3' blocking groups removed using strategies described in International patent publication WO2020097607A1 (Drmanac et al., 2020, "Massively parallel sequencing using unlabeled nucleotides").

Imaging Buffer

In one aspect of the invention, the imaging buffer is a buffered solution containing reduced L-glutathione and trolox. Optionally trolox may be excluded. L-Glutathione is a tripeptide comprising L-glutamic acid, L-cysteine, and glycine The concentration of reduced L-glutathione in the imaging buffer is generally in the range of 1-500 mM, more often 5-400 mM, such as 5-300 mM, 50-200 mM, or 90-110 mM. For example, the imaging buffer may comprise about 100 mM reduced L-glutathione.

Trolox is a water-soluble analog of vitamin E that acts as an antioxidant and scavenger of free radicals (PubChem. CID 40634; MW 250.294 g·mol$^{-1}$).

Trolox can be obtained from Sigma-Aldrich, TCI, and Cayman Chemical and other commercial suppliers.

Trolox together with glutathione can protect single-stranded DNA templates from laser-induced degradation when present in the imaging buffer at a range of concentrations, e.g., from about 0.1-20 mM, 0.1-1 mM, 1-2 mM, 2-3 mM, 3-4 mM, 4-5 mM, 5-6 mM, 6-7 mM, 7-8 mM, 8-9 mM, 9-10 mM, 1-10 mM, 10-20 mM, or about 1, 2, 3, 4, 5, 6, 7, 8, 9, 10, 11, 12, 13, 14, 15, 16, 17, 18, 19 or 20 mM. The imaging buffer may comprise 2 to 4 or about 4 mM of trolox. The concentration of trolox can be adjusted for a given DNA sequencing application, and in view of parameters such as the number of cycles performed, the nature of the laser(s) or other illumination sources used (such as power, and wavelength), the concentration of reduced L-glutathione and potentially other protective reagents in the imaging buffer, and the nature of the DNA template.

For example, the imaging buffer may comprise 100 mM reduced L-glutathione and 4 mM trolox. A complete buffered image solution might contain 1000 mM Tris (preset crystals) pH 8.2, 400 mM NaCl, 0.05% Tween-20 (a detergent), 4 mM trolox, and 100 mM reduced glutathione. Tween-20 is polyethylene glycol sorbitan monolaurate (CAS Number: 9005-64-5) and is commercially available (e.g., Sigma-Aldrich).

The imaging buffer may include reduced L-glutathione and trolox, in 50 mM 3-mercapto-1-propanesulfonate, 700 mM ammonium sulfate, 5% DMSO, and 450 mM Tris buffer, pH 9.

The imaging buffer used to protect the nucleic acid complex during the sequencing process typically comprises a buffering system to maintain a pH between about 7.5 and about 9. In embodiments the pH may be in a range from 7-10, preferably 8-10, such as 8-9. The imaging buffer may comprise reduced L-glutathione (for example, at a concentration of 100 mM) or L-glutathione and trolox in a buffered solution with a pH from about 7 to about 9, or at about 7-8, 8-9, 7.0-7.5, 7.5-8.0, 8.0-8.5, or 8.5-9.0. Suitable buffer systems include Tris (tris(hydroxymethyl)aminomethane), HEPES, or other buffers.

L-reduced glutathione can be synthesized or obtained from commercial sources. See, e.g., Lu (2013) Biochim Biophys Acta 1830(5):3143-3153 (describing biosynthesis).

There are four stereoisomers of glutathione. Commercially available glutathione is typically obtained from biological sources, so it almost always consists of the pure L-isomer alone and is preferred. However, other stereoisomers or mixtures thereof can be prepared by solid-phase chemical synthesis (T. Oikawa et al., J Nutr Sci Vitaminol (Tokyo) 1999; 45(2):223-9; Y. Hashizume et al., Anticancer Drugs. 2001 July; 12(6):549-54) and used in the present invention.

In some instances, imaging buffer containing reduced glutathione is substantially free of glutathione in the oxidized form. In this context, "substantially free" means at least 80% of glutathione in the buffer is reduced glutathione, at least 85%, at least 90%, at least 95%, or at least 99% of glutathione in the buffer is reduced glutathione.

Other Buffer Components and Compounds Excluded from the Imaging Buffer

In addition to reduced L-glutathione, trolox and a buffering system, one or more additional reagents may also be included in the imaging buffer to enhance protection or for other reasons. Examples are cysteine, N-acetyl cysteine (NAC), 2-mercaptoethanol, 2-mercaptoethylamine, trypanothione, mycothiol, methanethio, ethanethiol, 1-propanethiol, 2-propanethiol, allyl mercaptan, butanethiol, tert-butyl mercaptan, pentanethiols, thiopheno, dimercaptosuccinic, and thioacetic acid. NAC may be included at about 1-500 mM, more often 5-400 mM, such as 5-300 mM, 50-200 mM, 50-150 mM, or 10, 20, 30, 40, 50, 60, 70, 80, 90, 100, 110, 120, 130, 140, 150, 160, 170, 180, 190, or 200 mM may be included. Other compounds that can potentially be included in the imaging buffer include 3-mercapto-1-1-propanesulfonate, ammonium sulfate, or DMSO; anti-fade agents such as Fluoroguard™, Citifluor™, ProLong™, or SlowFade™, as well as compounds and additives known to provide a protective effect against DNA damage. Examples of such compounds include free radical scavenging agents, and others, and include, but are not limited to, ascorbic acid, dithiothreitol, mercaptoethylamine, β-mercaptoethanol, n-propyl gallate, p-phenylenediamine, hydroquinone, sodium azide, diazobicyclooctane, cyclooctatetraene, ergothioneine, methionine, N-tert-Butyl-α-phenylnitrone, caffeic acid, coumaric acid, chlorogenic acid, chlorophylin, delphinidin chloride, DL-α-lipoic acid, ellagic acid, eugenol, ferulic acid, formononetin, fucoxanthin, gallic acid, ginkgolide B, hesperidin, 3-hydroxytyrosol, kaempferol, linoleic acid, lipoic acid, luteolin, lysine, neochlorogenic acid, oleic acid, resveratrol, rutin hydrate, seleno-L-methionine, sodium selenite, tocopherol, xanthophyll, balsalazide disodium, bilirubin, cysteine, beta-dimethyl cysteine, butylated hydroxyl anisole, butylated hydroxytoluene, propyl gallate, tertiary butyl hydroquinone, nordihydroguaiaretic acid, mercaptopropionylglycine, MESNA, captopril, imidazole, polyphenols, carotenoids, flavonoids, catechins, carotene, lycopene, antheraxanthin, astaxanthin, canthaxanthin, neurosporene, rhodopin, bixin, norbixin, zeaxanthin, lutein, biliverdin, tocopherols, polyene dialdehydes, melatonin, vitamin E, vitamin B6, vitamin B6 analogs, hydrazine, sodium sulfite, hydroxylamine, histidine, tryptophan, ascorbic acid and gallic acid (gallate), or a combination of two or more of these.

In certain embodiments one, more than one, all, or any combination of the agents listed in the previous paragraph are specifically excluded from the Imaging Buffer. In one embodiment the imaging buffer does not contain ascorbic acid. In one embodiment the imaging buffer does not contain gallic acid. In one embodiment the imaging buffer does not contain NAC.

Signal Loss

Signal loss under various conditions can be compared in a variety of ways.

Illumination Vs No Illumination Method

In one approach signal loss under various conditions can be compared as described in the examples, below. Briefly, the intensity of fluorescence emission primer extension products produced from a clonal population of templates is measured following repeated cycles of illumination with excitation light followed by a terminal cycle or cycles of illumination. or without repeated cycles of illumination and only the terminal cycle or cycles of illumination. See Examples, FIGS. 1A and 1B, and Tables below. Where there is no difference between the intensity of fluorescence emission with and without repeated cycles of illumination there is no signal loss. Where the intensity of fluorescence emission (a) with repeated cycles of illumination is lower than fluorescence emission (b) without repeated cycles of illumination, the amount of signal loss can be expressed as a fraction, (a)/(b).

The protective effect of reduced L-glutathione and trolox, against illumination-mediated loss of fluorescence signal (i.e., accumulated signal loss resulting from illuminating the array) can be assessed by performing sequencing-by-synthesis using arrays (e.g., nanoarrays) comprising immobilized DNA nanoballs as templates: For example, using fluorescently labeled reversible terminators (RTs). In the assay, two nanoarrays are subjected to sequencing in parallel, under identical conditions except that one uses an imaging buffer comprising 5-200 mM (e.g., 100 mM) reduced L-glutathione, and the second uses an imaging buffer that is free of reduced L-glutathione. A specified number of sequencing cycles (perhaps 20) are performed. For both of the arrays (e.g., nanoarrays), a portion of the array is not illuminated in any of the cycles, and should therefore not undergo any illumination-mediated loss of signal. A second portion of the array, in contrast, is illuminated in each cycle and will therefore show a loss of signal that is associated with the cycles of illumination.

At the end of the specified number of cycles, for each array the entire array is illuminated and the fluorescence emission detected, and the loss of signal is determined by comparing the signal in the portion of the array that had been illuminated in each cycle (showing signal loss) with the signal in the portion of the array that had not been illuminated (representing possible non-illumination associated signal loss factors). The protective effect of reduced L-glutathione may be determined by comparing the signal loss differences in the array that was sequenced in the presence of reduced L-glutathione with the signal loss differences in the array that was sequenced in the absence of reduced L-glutathione. The assay may be performed with both reduced L-glutathione and trolox in the imaging buffer of a first array, and with neither reduced L-glutathione nor trolox in the imaging buffer in a second array.

Earlier Cycle Vs Later Cycle Method

In an another approach, signal loss can measure by comparing the intensity of fluorescence emission in a later cycle with the intensity of fluorescence emission in the same array in an earlier cycle. For example, the fluorescence emission of one or more fluorophores may be measured in the last of a specified number of sequencing cycles, and compared with the emission of the same fluorophore or fluorophores in the first sequencing cycle. The difference in signal between the first cycle and the later cycle reflects the extent of degradation of the DNA template that has taken place during the specified number of cycles.

DNA sequencing performed in the absence of reduced L-glutathione and trolox (or L-glutathione, and optionally trolox), may result in a decrease in the fluorescence signal after 20 cycles that is at least 2-fold the decrease occurring in DNA sequencing performed in the presence of reduced L-glutathione and optionally trolox. The signal measured in the presence of reduced L-glutathione and trolox (or L-glutathione, and optionally trolox), after 20 cycles may be 80%, 90%, or more of the signal observed in the first cycle.

Reduced Signal Loss and Increased Read Length

As illustrated in the Examples below, sequencing using an imaging buffer comprising reduced L-glutathione reduced signal loss. Without intending to be bound by a particular mechanism, the imaging buffer is believed to protect the template DNA and/or extended primer from damage or modification. Although damage to any single template or extended primer in a clonal population of templates may be rare, damage or modification accumulated over multiple cycles results in a reduction in the number of productive templates (templates from which fluorescence can be accurately measured). In addition, without intending to be bound by a particular mechanism, damaged or modified templates or extended primers may emit affect the net fluorescent signal profile that does not accurately reflect the template sequence.

In buffer assays the DNA sequencing is typically performed for at least 20 cycles, In practice the use of the imaging buffers disclosed herein allow accurate sequencing for much greater numbers of cycles, e.g., at least 50, 100, 150, 200, 300, 400, 500, 600, 700, 800, 1000 or 1500 cycles. The present methods will allow a greater number of cycles to be performed while maintaining a detectable signal than previously achieved.

As demonstrated in Example 1 (data shown in FIG. 2), average DNB intensity and the error rate are inversely related. This means that keeping the image intensity high with an imaging buffer according to this disclosure will help keep the accuracy of sequencing from eroding. This enables the user to perform longer sequence reads whilst helping to maintain accuracy.

Signal Loss Mechanism

Without intending to be bound by a particular mechanism, various types of damage may occur in the process of multiple sequencing cycles. The laser-induced degradation may result in signal loss due to cross-linking of the DNA to another substrate. The laser-induced degradation may result in signal loss due to cleavage of the DNA. The laser-induced degradation may result in signal loss due to loss of one or more bases within the DNA. The laser-induced degradation may result from direct effects of the illumination on the DNA or as an indirect result of fluorescence emission of the illumination dyes and production of free radicals or other chemical byproducts resulting from the illumination.

The degradation or modification of the DNA, including cross-linking of DNA to DNA, to the surface, or to proteins including polymerase, or the creation of abasic sites on the template DNA (single stranded or double stranded if the polymerase has exonuclease function), the extending strand, or both, can be detected by virtue of a progressive loss of fluorescence signal with an increasing number of sequencing cycles. With each cycle, the laser-mediated illumination of the reaction mixture may damage or cleave a certain proportion of the single-stranded DNA templates in the mixture, rendering the damaged or cleaved template unavailable for subsequent sequencing cycles and thereby decreasing the fluorescence emission signal.

Complementary Strand Synthesis

The damage or modification to DNA that can occur during the imaging step can affect template DNA, extending strands, and can also affect the synthesis of complementary DNA strands. For example, for sequencing the opposite end of a DNA template by cycles of nucleotide incorporation by polymerase, the complementary strand is made from the sequenced template. In one aspect of the invention, imaging buffer described herein is used during second strand or complementary strand synthesis.

One way to make the complementary strand uses controlled strand displacement methods (or second strand sequencing), as described in Example 2 below (generally as described in U.S. Pat. No. 10,227,647). Briefly, second-strand sequencing was done as follows: A DNB containing copies of adaptor sequence and inserted genomic DNA (concatemers of the adaptor-genomic DNA subunit) was hybridized with a primer for the first-end sequencing. After generating the first-end read, controlled, continued extension was performed by a strand displacing DNA polymerase to generate multiple complementary strands. When the 3' ends of the newly synthesized strands reach the 5' ends of the downstream strands, the 5' ends are displaced by the DNA polymerase generating single stranded DNA overhangs, and creating a branched DNB structure. A second-end sequencing primer was hybridized to the adaptor copies in the newly created branches to generate a second-end read.

For DNBs, a related way to do this is by synchronized controlled multiple displacement amplification (MDA). For MDA to be able to make the needed DNA branches, and especially for longer templates (e.g. 300-500 bases or 400-700 bases, or 500-1000 bases), the polymerase has to copy about 1000 to 2000 bases or 2000 to 4000 bases of the concatenated template with adapters. If there are frequent polymerase blocks (such as nicks or cross-links) introduced by the effects of fluorescent imaging, the branch creation may be terminated prematurely, thereby reducing the amount of complementary template created.

Buffers and Kits

Reaction mixtures, imaging buffers, and kits comprising the imaging buffers are contemplated. For example, an imaging buffer for use in DNA sequencing is may include reduced L-glutathione and trolox, wherein the pH of the buffer is in the range from about 7.5 to about 9.0.

A kit may comprise a first container, or a plurality of first containers, containing an imaging buffer, and one or more additional containers containing other reagents or useful for DNA sequencing, such as fluorescent dyes, enzymes, nucleotides, nucleotide analogs (such as reversible terminators), antibodies, and/or solid supports. A kit for the imaging buffer may contain the components in solution, or as solid phase reagents that are reconstituted with aqueous or other solvents before use. In other formats the kit imaging buffer may be in a higher concentrated form that is diluted with water or other solvents before use. In other formats some of the components may be pre-combined and some components of the imaging buffer may be added to the pre-combined components before use. A sequencing kit may comprise a container of imaging buffer and other containers of reagents for sequencing such as wash buffers, reversible terminator regeneration reagents, polymerase and reversible terminator nucleotides. Kit reagents may be pre-combined, or provided separately to be combined just before use.

EXAMPLES

Methods

Arrays were loaded with single-stranded DNA nanoballs (DNBs) containing either *E. coli* or human precut genomic DNA. In example 1 below, imaging tests were done using MGI's patterned arrays with a pitch size of 900 nm and with approximately 200 nm binding regions (e.g., BGISEQ-500RS™ High-throughput sequencing kit (PN: 85-05238-01, BGI)). In subsequent examples, the reagents were from the DNBSEQ-G400RS™ High-throughput Sequencing Set (FCL PE100) Item No. 1000016950, MGI Tech Co., Ltd.

Example 1. Evaluating Signal Loss in the Presence or Absence of Reduced L-Glutathione This example shows that inclusion of reduced L-glutathione in an imaging buffer reduces accumulated signal loss resulting from damage to the DNA template.

Twenty cycles of sequencing-by-synthesis were carried out using the DNB templates and fluorescently labeled reversible terminator nucleotides. The reversible terminator nucleotides had a fluorescent dye attached via a cleavable-linker nucleobase and a blocking moiety at the 3'-OH position of ribose. Four colored dyes were used representing the four bases. The terminators were a mixture of azidomethyl and disulfide.

In each cycle, following incorporation of the reversible terminator nucleotides using DNA polymerase, polymerase and unincorporated nucleotides were washed away by flooding the array with a wash buffer before adding an imaging buffer or a control buffer at 50° C. The imaging buffer was 50 mM 3-mercapto-1-propanesulfonate, 700 mM ammonium sulfate, 5% DMSO, 450 mM Tris buffer, pH 9 with reduced L-glutathione. The control buffer was 50 mM 3-mercapto-1-propanesulfonate, 700 mM ammonium sulfate, 5% DMSO, 450 mM Tris buffer, pH 9.

Some sites of the array flow-cell lane were exposed to laser light and imaged after each incorporation cycle and the remainder of sites were not exposed to the laser light. At the end of a designated number of cycles, the entire slide lane was then re-imaged after a final incorporation cycle to calculate and compare the signal loss of the light exposed regions in the presence or absence of reduced L-glutathione. The imaging instrument used was MGISeq 500™, and the exposure time was 130 msec, which was more than 3-fold that of the 40 msec exposure time that is regularly used with this sequencing instrument. A longer exposure time was used to promote light effects, if they were occurring. Following each cycle the dye and blocking groups were removed with the phosphine THPP.

Figure 1A:
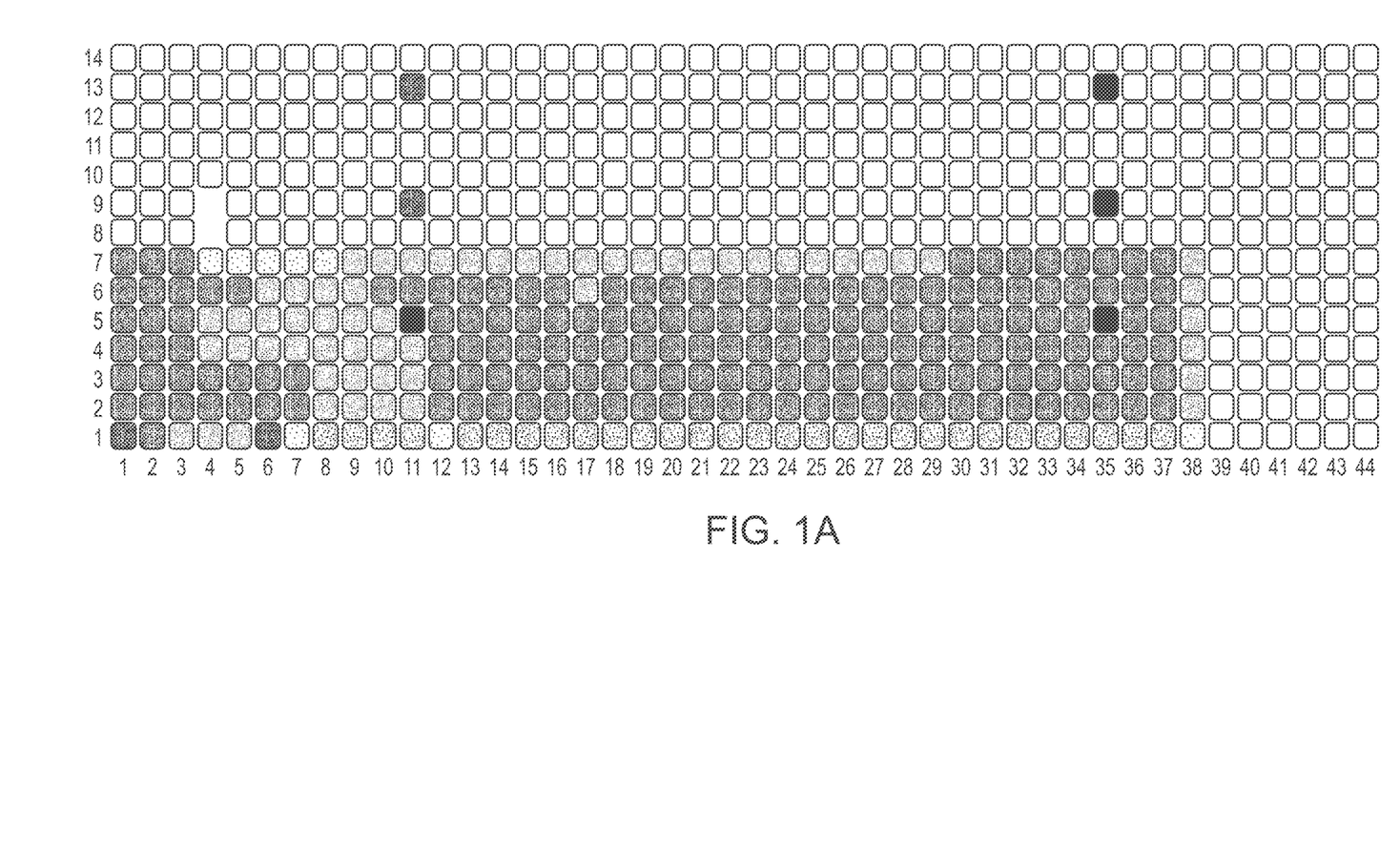
Figure 1B:
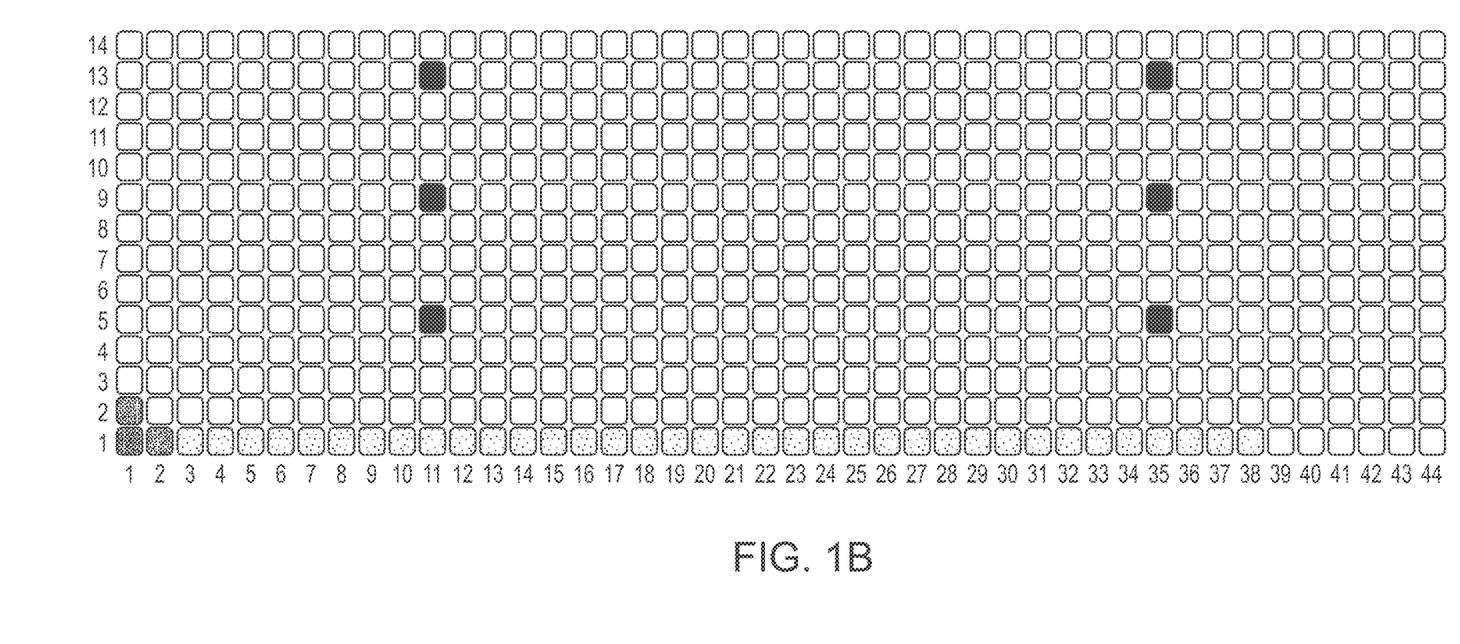

FIGS. 1A and 1B show the results. The depiction is a graduated density representation of imaged field intensities in a flow cell lane. Part of the surface area of a BGI-SEQ-500™ flow cell is represented as a matrix of fields ordered in rows and columns with each field represented as a rounded square. In each cycle fluorescently labeled reversible terminator nucleotides were incorporated at each site. However, only rows 1 to 7 and columns 1 to 38 were exposed to laser light at the excitation wavelengths (approximately 532 nm and 660 nm) of the fluorescent dyes for 130 msec for purposes of imaging during each cycle of the process. The other fields were only exposed to the laser light on the final cycle, thereby providing a baseline for signal in the absence of template damage. Intensity levels were extracted from the raw pixel intensity levels of captured images.

Intensities were aggregated by computer for each base-dye type for each field and expressed as "Rho" intensity for each imaging field of multiple DNBs. (Measuring fluorescence emission for each individual spot or DNB in a DNB array should give similar results, although intensity values could be influenced by neighbor spots and sequence context.) Each square represents the Rho value Intensity levels and were scaled with open squares representing higher intensities and more densely stippled squares representing lower intensities. The six solid-fill (or red) squares in each panel are markers for positioning and interpreting the image obtained. There are two missing squares in FIG. 1A: when some field squares are unable to be registered correctly due to dust, bubbles, or other interference, then no data is reported for that square.

FIG. 1A shows the effect of imaging at 50° C. in control buffer for 20 cycles. There was a 40-50% decrease in average image intensity for the sites illuminated with laser light in each cycle compared with fields illuminated with laser light in only the final cycle.

FIG. 1B shows the effect of imaging at 50° C. in imaging buffer (including 100 mM reduced L-glutathione) for 20 cycles in the imaging buffer. Under these conditions there was a 4-10% decrease in average image intensity in the fields illuminated with laser light in each cycle compared with fields illuminated with laser light in only the final cycle.

These results indicate that inclusion of reduced L-glutathione in an imaging buffer reduces accumulated signal loss resulting from effects on the DNA template, extending strand, or both.

Figure 2:
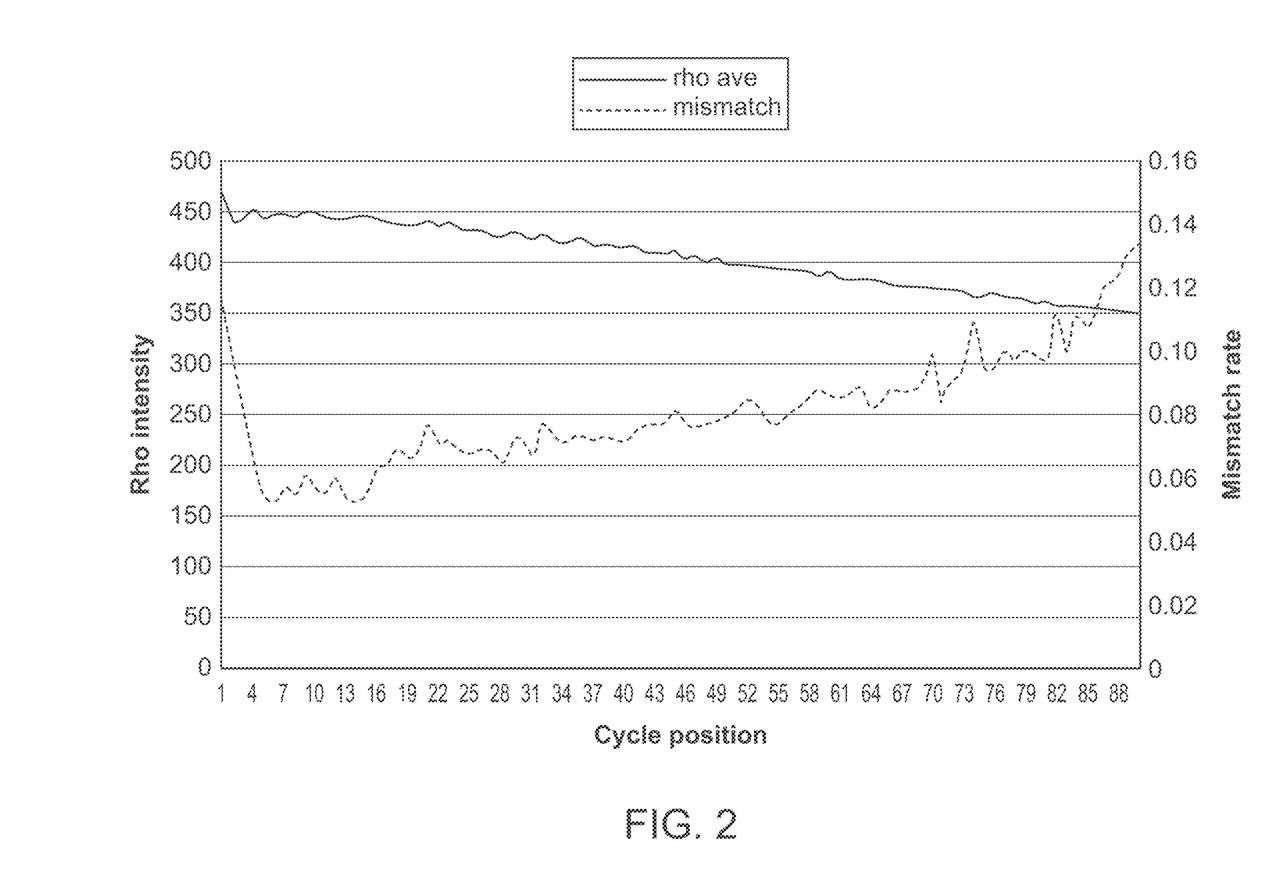
FIG. 2 shows data correlating the mismatch rate (or error rate) over 90 cycles of sequencing, compared with the change in Rho intensity over the same cycles.

FIG. 2 is a graph of data correlating the mismatch rate (or error rate) over 90 cycles of sequencing, compared with the change in Rho intensity over the same cycles. To obtain this data, DNBs that had been generated from an *E. coli* DNA library were sequenced on an MGIseq-2000 instrument for 90 cycles using a standard (not glutathione) buffer. The sequence reads from five fields were mapped to an *E. coli* reference database to identify reads with positions that mismatched to the expected basecall at that position of the read. The percentage of basecalls at each position that are discordant with the reference are shown. For the same fields the average rho intensity was determined for each base at each position, and then the average of the 4 bases was determined for each position.

The data show that the image intensity and the error rate are inversely related. This means that keeping the image intensity high with an imaging buffer according to this disclosure will help prevent the accuracy of sequencing from eroding. This enables the user to perform longer sequence reads by preserving accuracy.

Example 2. Reduced L-Glutathione at DH 8.2

This experiment assessed whether reduced L-glutathione in combination with Trolox is effective at protecting DNA and thereby preventing loss of image intensity at pH 8.2. Imaging conditions were on the MGISEQ-2000 sequencing platform and were of similar conditions as the BGISEQ-500 platform used in Example 1. The exposure times were typically 40 ms.

Controlled strand displacement methods (or second strand sequencing), generally as described in U.S. Pat. No. 10,227,647, were used to make and sequence second strands. Briefly, second-strand sequencing was done as follows: A DNB containing copies of adaptor sequence and inserted genomic DNA (concatemers of the adaptor-genomic DNA subunit) was hybridized with a primer for the first-end sequencing. After generating the first-end read, controlled, continued extension was performed by a strand displacing DNA polymerase to generate multiple complementary strands. When the 3' ends of the newly synthesized strands reach the 5' ends of the downstream strands, the 5' ends are displaced by the DNA polymerase generating single stranded DNA overhangs, and creating a branched DNB structure. A second-end sequencing primer was hybridized to the adaptor copies in the newly created branches to generate a second-end read.

Results are shown in Tables 1A and 1B below. Rho intensity is an average intensity representation of emitted light from the four fluorescent dyes for groupings of DNBs based upon their tendency to be grouped in intensity space by virtue of the predominately incorporated base in each DNB. Multiple DNBs in an intensity group produces a single Rho value representative of the group of DNBs.

In the top half of each table, samples were all treated with sequencing reagents for 95 cycles (SE95). Sites exposed to light at the excitation wavelength for all 95 cycles of sequencing were compared with sites treated the same way but only exposed to light for an additional 5 cycles. After 100 cycles and second strand making, a primer was annealed to the other strand and extended in the reverse direction for 5 cycles (PE5).

In Table 1A, the flow cell containing reduced L-glutathione contained 100 mM reduced L-glutathione and 4 mM trolox, pH 8.2. The difference in average intensity from the DNBs that had been pre-imaged for 95 cycles ("SE95", Col. 48) and those imaged for a final 5 cycles (Col. 49) was in the range of about 4.9% to 6.8%. This was very similar to or better than the standard condition flow cell that was imaged in the presence of imaging reagent (IR) "Vitamin C IR", which includes Vitamin C, 2 mM trolox, 5 mM gallic acid, and 5 mM dithiothreitol (Table 1B). The Vitamin C IR buffer was a previous imaging buffer, used in this experiment for comparison.

TABLE 1A

TROLOX AND GLUTATHIONE

| 4 mM Trolox + 100 mM glutathione pH 8.2 46188 | Rho average | A | C | G | T |
| --- | --- | --- | --- | --- | --- |
| SE95 | Column 48 | 267.69 | 284.47 | 212.18 | 189.45 |
|  | Column 49 | 285.88 | 298.53 | 223.59 | 199.69 |
|  | Difference | 18.18 | 14.07 | 11.41 | 10.25 |
|  | Difference | 6.79% | 4.94% | 5.38% | 5.41% |
| PE5 | Column 48 | 705.87 | 750.33 | 593.08 | 530.19 |
|  | Column 49 | 727.79 | 768.97 | 622.13 | 554.29 |
|  | Difference | 21.92 | 18.64 | 29.05 | 24.10 |
|  | Difference | 3.11% | 2.48% | 4.90% | 4.55% |

TABLE IB

| Standard Vitamin C IR 47297 | Rho average | A | C | G | T |
| --- | --- | --- | --- | --- | --- |
| SE95 | Column 48 | 319.68 | 308.01 | 234.44 | 223.38 |
|  | Column 49 | 340.65 | 328.79 | 249.82 | 235.76 |
|  | Difference | 20.97 | 20.78 | 15.38 | 12.38 |
|  | Difference | 6.56% | 6.75% | 6.56% | 5.54% |
| PE5 | Column 48 | 834.68 | 858.74 | 674.36 | 622.17 |
|  | Column 49 | 865.1 | 892.13 | 706.43 | 647.98 |
|  | Difference | 30.42 | 33.39 | 32.07 | 25.81 |
|  | Difference | 3.64% | 3.89% | 4.76% | 4.15% |

With respect to the image intensity from the second strand sequencing ("PE5"), the area of the flow cell exposed to imaging for 95 cycles (95 cycles of the first strand, followed by another 5 cycles first strand and 5 cycles of the second strand) showed an about 2.5% to 4.9% difference between the non-imaged and imaged areas when reduced L-glutathione was used. This was better than the standard control flow cell, which showed a 3.6 to 4.7% difference between the imaged and non-imaged areas. The damage during imaging that impacts second stand sequencing is reflected in the ability of polymerase to generate the second strand and is minimized by reduced L-glutathione at pH 8.2 to a degree similar to Vitamin C.

In other words, there are two read-outs of the effect of fluorescent imaging: a decrease of intensity during 95 cycles of sequencing of the first strand, and a decrease of intensity after crossing over to the second strand. In both cases, a buffer containing both glutathione and trolox helps protect against progressive loss of intensity during multiple cycles of sequencing. The two readouts are different in several ways. Different polymerases are used, one for reversible terminator incorporation and the other for strand displacement amplification. Both processes rely on functional extendable primers and intact template strands, but each process may rely upon those elements to differing degrees. The demonstrated benefit of glutathione and trolox to both processes shows the utility and benefit of the additives to multiple aspects of the sequencing process.

Example 3. Imaging Buffer Containing N-Acetyl-Cysteine (NAC) and Trolox

We demonstrated that N-acetyl cysteine (NAC) in combination with trolox also protects DNA from damage observed in multiple sequencing cycles.

This experiment shows that light protective properties of NAC were improved when compared to analysis using imaging buffer without protective additives. Intensity differences between imaged and non-imaged areas when no additives were present could be about 50% over 100 cycles of sequencing (i.e., half the intensity is observed in imaged areas as non-imaged areas).

When reducing agents such as trolox and dithiothreitol were added, the intensity difference could be reduced to just a 15% difference between imaged and non-imaged areas of the first strand sequencing. However, intensity from second strand sequencing was still 30% lower in the imaged area compared with the non-imaged area. DTT was used for comparison as a frequently used component of imaging buffer. In these experiments, GSH plus trolox generally performed better than NAC plus trolox.

After approximately 95 cycles of first strand sequencing-by-synthesis of DNBs in which only a portion of the flow cell lane was imaged, the sequencing area was expanded to include an area that was previously not imaged (and therefore not exposed to light). Cycles of first strand sequencing continued for about 5 cycles to determine imaged versus non-imaged area intensities before preparing the second strand for sequencing. In this process, the strand created during first strand sequencing was further extended by an added polymerase and additional second strands were created from added primers with the eventual creation of branched second strands that, due to the displacement properties of the polymerase, were in a single-stranded state.

Sequencing of the second strands was done by adding primers that hybridize to the second strand and sequencing continued with the expanded area of flow cell imaging. Damage or modifications to the template DNB strand, or the extending strand, during the initial 95 cycles of light-exposed sequencing cycles could affect the ability to make sufficient second strand and this damage would be expected to be reflected in the intensity levels observed for second strand sequencing based upon the exposure during the initial 95 cycles.

When imaging buffer containing 100 mM NAC plus trolox at pH 8.2 was used, about an 8% difference was observed in the imaged versus non-imaged areas of the flow cell and about a 6% difference in the imaged versus non-imaged areas on the second strand.

These data show that NAC contributed to the protection of the DNA, resulting in slower rates of intensity loss and offering protection that allowed more efficient generation of the second strand for second strand sequencing.

NAC, when added to the imaging buffer, can also protect the DNA. This effect occurs in a range of pH values of 7 to 9 but was generally favored at higher pH (e.g., pH 8-10, pH 8-9.5, pH 8.5-9). For example, using imaging buffer containing 150 mM NAC at pH 7, we observed about a 1.2 fold increase in second strand intensity over first strand intensity, compared to a 1.9 fold increase in $2^{nd}$ strand intensity over first strand intensity when imaging buffer contained 150 mM NAC at pH 9.

The intensity loss and second strand recovery was compared using two flow cells, one that used 50 mM NAC in the imaging buffer at pH 9 and one that used Vitamin C in the imaging buffer pH 7. The average second strand recovery was similar for the imaging buffer containing NAC compared with results using Vitamin C (1.91 vs 1.86-fold recovery respectively). Rates of intensity loss at between 0.4 to 0.5% loss per cycle were also similar between the two conditions. These two observations demonstrate that N-acetyl cysteine can substitute for Vitamin C in light-related imaging protection during sequencing.

Example 4. Glutathione and NAC Together

Both reduced L-glutathione and NAC alone or in combination with other protecting agents (e.g., trolox and dith-iothreitol, DTT) or other additives in the imaging buffer show good DNA protection, including at high temperature (e.g. 57° C.) imaging. In some experiments at pH 8.2, reduced L-glutathione was found to be better than NAC. At higher temperatures, better protection is achieved in a higher (more basic) pH (e.g. pH 9 is better than pH 7).

For imaging at lower temperatures (e.g. 15-40° C.), reduced L-glutathione provided similar protection for a wider pH range, e.g., in the range from pH 7 to pH 9 or pH 8 to pH 9. The protective range of concentrations is 20-200 mM, more preferably 50-150 mM.

Example 5. Comparison of Ingredients in the Imaging Buffer

To further characterize the benefit of additives in the imaging buffer, laboratory work was done to examine the effect of multi-cycle light exposure to a select number of imaging fields in the lanes of an MGIseq2000™ sequencing flow cell. All fields of the flow cell receive sequencing reagents but there is the option to expose a field to light during the image collection step of a sequencing cycle, or not.

Table 2 shows results obtained using an imaging buffer that contained neither glutathione nor trolox. Intensity values and differences for each of the sequenced bases A, C, G or T (Rho intensity is an average intensity representation of groups of DNBs). Column 48 refers to a group of fields that were imaged, and column 49 refers to a group of fields nearby but not imaged. In the upper panel, fields were exposed to 95 cycles of sequencing (SE95), and differential imaging before undergoing whole lane imaging and second strand synthesis followed by a further 5 cycles (PE5) of sequencing on the second strand. The difference in intensities between the imaged and non-imaged fields is shown.

TABLE 2

| (buffer containing no protecting reagents) | | Rho average | A | C | G | T |
|---|---|---|---|---|---|---|
| SE95 | Column 48 | 447.3 | 427.73 | 331.64 | 317.53 |
| | Column 49 | 515.9 | 447.99 | 383.54 | 360.265 |
| | Difference | 68.6 | 20.26 | 51.9 | 42.735 |
| | Difference | 15.34% | 4.74% | 15.65% | 13.46% |
| PE5 | Column 48 | 1380.5 | 1186.2 | 918.77 | 966.97 |
| | Column 49 | 1777 | 1536.8 | 1178.75 | 1244.53 |
| | Difference | 396.5 | 350.6 | 259.98 | 277.56 |
| | Difference | 28.72% | 29.56% | 28.30% | 28.70% |

The data in Table 2 compare intensity values for each of the sequenced bases A, C, G or T between fields exposed to imaging or no-imaging for 95 cycles of sequencing in a non-glutathione or non-Vitamin C containing buffer. In general, all buffers contained 1000 mM Tris (Tris(hydroxymethyl) aminomethane), 400 mM NaCl and 0.05% Tween-20. Tween-20 is polyethylene glycol sorbitan monolaurate (CAS Number: 9005-64-5) and is commercially available (e.g., Sigma-Aldrich). The differences in intensity between imaged and non-imaged areas can be up to 15.65% after the first strand sequencing of 95 cycles. This difference can increase to 29.56% for the difference of intensity on the second strand sequencing. Imaging buffer containing reduced glutathione/trolox or Vitamin C/trolox was typically less than 6% difference between imaged and non-imaged areas (Table 3 and Table 4). This indicates that glutathione or vitamin C, each in combination with trolox, can produce protective effects against intensity loss relative to an imaging buffer with no preservation reagents.

Table 3 shows results from reduced glutathione (100 mM), trolox (4 mM), pH 8.2 imaging buffer. Intensity values and differences for each of the sequenced bases A, C, G or T (Rho intensity is an average intensity representation of groups of DNBs). Column 48 refers to a group of fields that were imaged and column 49 refers to a group of fields nearby but not imaged. In the upper panel, fields were exposed to 95 cycles of sequencing (SE95) and differential imaging before undergoing whole lane imaging and second strand synthesis followed by a further 5 cycles (PE5) of sequencing on the second strand. The difference in intensities between the imaged and non-imaged fields is shown.

TABLE 3

| 4 mM Trolox + 100 mM glutathione pH 8.2 | Rho average | A | C | G | T |
|---|---|---|---|---|---|
| SE95 | Column 48 | 227.32 | 209.97 | 149.78 | 169.95 |
| | Column 49 | 239.5 | 218.41 | 155.98 | 177.32 |
| | Difference | 12.18 | 8.44 | 6.2 | 7.37 |
| | Difference | 5.36% | 4.02% | 4.14% | 4.34% |
| PE5 | Column 48 | 514.63 | 561.2 | 419.78 | 384.48 |
| | Column 49 | 531.31 | 578.85 | 431.26 | 396.72 |
| | Difference | 16.68 | 17.65 | 11.48 | 12.24 |
| | Difference | 3.24% | 3.15% | 2.73% | 3.18% |

Table 4 shows the results of imaging buffer with Vitamin C. Intensity values and differences for each of the sequenced bases A, C, G or T (Rho intensity is an average intensity representation of groups of DNBs). Column 48 refers to a group of fields that were imaged and column 49 refers to a group of fields nearby but not imaged. In the upper panel, fields were exposed to 95 cycles of sequencing (SE95) and differential imaging before undergoing whole lane imaging and second strand synthesis followed by a further 5 cycles (PE5) of sequencing on the second strand. The difference in intensities between the imaged and non-imaged fields is shown.

TABLE 4

| Standard Vitamin C IR | Rho average | A | C | G | T |
|---|---|---|---|---|---|
| SE95 | Column 48 | 212.44 | 177.93 | 130.35 | 142.93 |
| | Column 49 | 227.02 | 188.97 | 138.82 | 152.49 |
| | Difference | 14.58 | 11.04 | 8.47 | 9.56 |
| | Difference | 6.86% | 6.20% | 6.50% | 6.69% |
| PE5 | Column 48 | 489.81 | 513.37 | 381.2 | 364.88 |
| | Column 49 | 507.46 | 534.73 | 394.75 | 379.7 |
| | Difference | 17.65 | 21.36 | 13.55 | 14.82 |
| | Difference | 3.60% | 4.16% | 3.55% | 4.06% |

Inclusion of trolox gives added benefit as shown below when comparing data from Table 5 with Table 3. Reduced glutathione without added trolox (Table 5) showed intensity differences of 7.21% to 11.8% and with similar differences after second strand making. Glutathione with trolox showed differences between imaged/no-imaged areas of less than 6% (Table 3).

Table 5 shows results of reduced glutathione imaging buffer pH 8.2 without trolox. Intensity values and differences for each of the sequenced bases A, C, G or T (Rho intensity is an average intensity representation of groups of DNBs). Column 48 refers to a group of fields that were imaged and column 49 refers to a group of fields nearby but not imaged. In the upper panel, fields were exposed to 95 cycles of sequencing (SE95) and differential imaging before undergoing whole lane imaging and second strand synthesis followed by a further 5 cycles (PE5) of sequencing on the second strand. The difference in intensities between the imaged and non-imaged fields is shown.

TABLE 5

| 100 mM glutathione pH 8.2 | Rho average | A | C | G | T |
|---|---|---|---|---|---|
| SE95 | Column 48 | 220.46 | 181.11 | 132.41 | 144.70 |
| | Column 49 | 241.46 | 201.73 | 148.04 | 155.13 |
| | Difference | 21.00 | 20.62 | 15.63 | 10.43 |
| | Difference | 9.53% | 11.39% | 11.80% | 7.21% |
| PE5 | Column 48 | 623.39 | 606.28 | 436.81 | 427.53 |
| | Column 49 | 668.04 | 651.83 | 488.68 | 470.59 |
| | Difference | 44.65 | 45.55 | 51.87 | 43.06 |
| | Difference | 7.16% | 7.51% | 11.87% | 10.07% |

A lower pH of 7.2 (Table 6) increased differences between imaged and non-imaged areas with 33%-42% differences on first strand sequencing and around 60% difference for second strand sequencing suggesting less protective effect of glutathione at the lower pH. Decreasing the concentration of glutathione to 25 mM from 100 mM showed a small increase in differences between imaged and no image areas as shown in data from Table 3 and Table 7. First strand differences were around 6-7% with 25 mM glutathione compared with 4-5% with 100 mM glutathione.

Table 6 shows results of an imaging buffer comprising reduced glutathione buffered at pH 7.2. Intensity values and differences for each of the sequenced bases A, C, G or T (Rho intensity is an average intensity representation of groups of DNBs). Column 48 refers to a group of fields that were imaged and column 49 refers to a group of fields nearby but not imaged. In the upper panel, fields were exposed to 95 cycles of sequencing (SE95) and differential imaging before undergoing whole lane imaging and second strand synthesis followed by a further 5 cycles (PE5) of sequencing on the second strand. The difference in intensities between the imaged and non-imaged fields is shown.

TABLE 6

| 100 mM glutathione pH 7.2 36108 | Rho average | A | C | G | T |
|---|---|---|---|---|---|
| SE95 | Column 48 | 145.47 | 94.47 | 86.59 | 94.83 |
| | Column 49 | 196.81 | 131.56 | 12.2.98 | 126.29 |
| | Difference | 51.34 | 37.09 | 36.39 | 31.46 |
| | Difference | 35.29% | 39.26% | 42.03% | 33.18% |
| PE5 | Column 48 | 274.10 | 263.77 | 270.51 | 221.40 |
| | Column 49 | 446.64 | 424.26 | 429.28 | 348.37 |
| | Difference | 172.54 | 160.49 | 158.77 | 126.97 |
| | Difference | 62.95% | 60.84% | 58.69% | 57.35% |

Table 7 shows results of a reduced glutathione (25 mM) imaging buffer. Intensity values and differences for each of the sequenced bases A, C, G or T (Rho intensity is an average intensity representation of groups of DNBs). Column 48 refers to a group of fields that were imaged and column 49 refers to a group of fields nearby but not imaged. In the upper panel, fields were exposed to 95 cycles of sequencing (SE95) and differential imaging before undergoing whole lane imaging and second strand synthesis followed by a further 5 cycles (PE5) of sequencing on the second strand. The difference in intensities between the imaged and non-imaged fields is shown.

TABLE 7

| 4 mM Trolox + 25 mM glutathione pH 8.2 | Rho average | A | C | G | T |
|---|---|---|---|---|---|
| SE95 | Column 48 | 194.68 | 172.79 | 121.17 | 133.04 |
|  | Column 49 | 209.37 | 185.39 | 130.95 | 142.88 |
|  | Difference | 14.69 | 12.6 | 9.78 | 9.84 |
|  | Difference | 7.55% | 7.29% | 8.07% | 7.40% |
| PE5 | Column 48 | 382.17 | 421.61 | 301.8 | 286.24 |
|  | Column 49 | 403.8 | 447.83 | 323.23 | 304.62 |
|  | Difference | 21.63 | 26.22 | 21.43 | 18.38 |
|  | Difference | 5.66% | 6.22% | 7.10% | 6.42% |

Examples Data Summary

The data in Tables 1A to 7 above may be approximated and summarized as shown in Table 8.

TABLE 8

| Table | Conditions | signal loss after 95 sequencing cycles (SE95) | signal loss for opposite strand synthesis (PE5) |
|---|---|---|---|
| 1A | 4 mM Trolox; 100 mM glutathione, pH 8.2 | 6% | 3% |
| 1B | Vitamin C IR | 6% | 7% |
| 2 | (no protective agent) | 14% | 29% |
| 3 | 4 mM Trolox; 100 mM glutathione, pH 8.2 | 5% | 3% |
| 4 | Vitamin C IR | 7% | 4% |
| 5 | 100 mM glutathione, pH 8-2 (no Trolox) | 10% | 9% |
| 6 | 4 mM Trolox; 100 mM glutathione, pH 7.2 | 38% | 60% |
| 7 | 4 mM Trolox; 25 mM glutathione, pH 8.2 | 7% | 6% |

Under these reaction conditions, the combination of 4 mM Trolox and 100 mM glutathione at pH 8.2 lowered signal loss in the first strand from 14% to 6% (a 57% improvement), and in the second strand from 29% to 3% (a 90% improvement) (Tables 1A and 3, compared with Table 2). The presence of trolox in combination with the glutathione was 40% better and 66% better, respectively, in preventing signal loss in first and second strand synthesis, compared with glutathione alone (Table 5). The benefit of glutathione was lost when used outside the working pH range (Table 6), but was mostly retained when the glutathione was lowered in concentration to 25 mM (Table 7).

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

The invention claimed is:

1. A method of nucleic acid sequencing-by-synthesis, the method comprising carrying out at least 20 nucleic acid sequencing cycles using an array comprising immobilized DNA templates, wherein each cycle comprises:
   i) incorporating reversible terminator nucleotides into a plurality of extended primers on the array, wherein fluorescent dye molecules are associated with the incorporated reversible terminator nucleotides before or after incorporation, whereby the fluorescent dye molecules are associated with the templates and extended primers;
   ii) contacting the array with an imaging buffer comprising trolox and 5 to 200 mM reduced glutathione;
   iii) illuminating the array to induce fluorescent emission from the fluorescent dye molecules and detecting the fluorescent emission; then
   iv) removing the imaging buffer and the fluorescent dye molecules from the DNA templates on the array.

2. The method of claim 1, wherein the concentration of trolox in the Imaging imaging buffer is 2 to 4 mM.

3. The method of claim 1 wherein the imaging buffer is buffered at a pH of from 7.5 to 9.0.

4. The method of claim 1, wherein the fluorescent dye molecules are conjugated directly to the incorporated reversible terminator nucleotides.

5. The method of claim 1, wherein the immobilized DNA templates are DNA nanoballs (DNBs) each having multiple copies of a template sequence.

6. The method of claim 1, wherein each of the immobilized DNA templates is a clonal cluster of DNA strands each having a single copy of a template sequence.

7. The method of claim 1, wherein in step (iv) removing the imaging buffer and removing the fluorescent dye molecules occur at the same time.

8. The method of claim 1, whereby after the $20^{th}$ sequencing cycle, the fluorescent emission from the extended primers in the imaging buffer has not decreased to the extent it would be without the imaging buffer.

9. The method of claim 1, wherein the fluorescent emission measured in the $20^{th}$ sequencing cycle is at least 90% of the emission measured in the first cycle.

10. The method of claim 1, wherein a decrease in the fluorescent emission measured in the $20^{th}$ sequencing cycle relative to the emission in the first cycle in the presence of said imaging buffer is less than 50% the decrease measured in the $20^{th}$ sequencing cycle relative to the emission in the first cycle in the absence of said imaging buffer.

11. A method of nucleic acid sequencing-by-synthesis, said method comprising carrying out at least 20 nucleic acid sequencing cycles using an array comprising immobilized DNA templates on the array, wherein each cycle comprises:
   i) incorporating reversible terminator nucleotides that do not have directly conjugated fluorescent dye molecules into a plurality of growing strands on the array;
   ii) binding fluorescent dye molecules to the reversible terminator nucleotides using a specific antibody or other affinity reagent;
   iii) contacting the array with an imaging buffer comprising 5 to 200 mM reduced glutathione at a pH of from 7.5 to 9.0;
   iv) illuminating the array to induce fluorescent emission from the fluorescent dye molecules and detecting the fluorescent emission; then
   v) removing the imaging buffer and the fluorescent dye molecules from the DNA templates on the array.

12. An imaging buffer configured for use in preserving emission intensity during sequencing-by-synthesis using fluorescent dyes, the buffer containing 2 to 4 mM trolox and 5 to 200 mM reduced glutathione, buffered at a pH of from 7.5 to 9.0.

13. The imaging buffer of claim 12 comprising 4 mM trolox and 100 mM reduced glutathione, buffered at a pH 7.5-9.0.

14. The imaging buffer of claim 13 comprising 1000 mM Tris, 400 mM NaCl, 0.05% polyethylene glycol sorbitan monolaurate, 4 mM trolox, and 100 mM reduced glutathione, buffered at a pH 7.5-9.0.

15. The imaging buffer of claim 13, buffered at a pH of about 8.2.

16. A method of improving nucleic acid sequencing to sustain emission intensity of fluorescent dyes used in the sequencing through multiple cycles of sequencing, wherein said method comprises carrying out at least 20 nucleic acid sequencing cycles using an array comprising immobilized DNA templates on the array, wherein each cycle comprises:
   a) incorporating reversible terminator nucleotides into a plurality of growing strands on the array, wherein fluorescent dye molecules are associated with the incorporated reversible terminator nucleotides before or after incorporation, and
   b) illuminating the array to induce fluorescent emission from the fluorescent dye molecules and detecting the fluorescent emission;
   wherein the improving comprises conducting the illuminating and optionally the incorporating in an imaging buffer according to claim 13.

* * * * *

UNITED STATES PATENT AND TRADEMARK OFFICE
CERTIFICATE OF CORRECTION

| | | |
|---|---|---|
| PATENT NO. | : 11,761,040 B2 | Page 1 of 1 |
| APPLICATION NO. | : 17/600826 | |
| DATED | : September 19, 2023 | |
| INVENTOR(S) | : Snezana Drmanac, Matthew J. Callow and Radoje T. Drmanac | |

It is certified that error appears in the above-identified patent and that said Letters Patent is hereby corrected as shown below:

In the Claims

In Column 22, Line 21, Claim 2:
Delete "trolox in the Imaging imaging buffer is 2 to 4 mM" and
Insert -- trolox in the imaging buffer is 2 to 4 mM --.

Signed and Sealed this
Twenty-sixth Day of December, 2023

Katherine Kelly Vidal
Director of the United States Patent and Trademark Office